(12) United States Patent
Ruff

(10) Patent No.: US 7,806,908 B2
(45) Date of Patent: *Oct. 5, 2010

(54) BARBED TISSUE CONNECTOR

(75) Inventor: Gregory L. Ruff, Chapel Hill, NC (US)

(73) Assignee: Quill Medical, Inc.

( * ) Notice: Subject to any disclaimer, the term of this patent is extended or adjusted under 35 U.S.C. 154(b) by 333 days.

This patent is subject to a terminal disclaimer.

(21) Appl. No.: 11/968,494

(22) Filed: Jan. 2, 2008

(65) Prior Publication Data

US 2008/0221617 A1 Sep. 11, 2008

Related U.S. Application Data

(63) Continuation of application No. 11/747,085, filed on May 10, 2007, which is a continuation of application No. 10/420,119, filed on Apr. 21, 2003, now Pat. No. 7,226,468, which is a continuation of application No. 09/629,428, filed on Jul. 31, 2000, now abandoned, which is a continuation of application No. 08/324,529, filed on Oct. 18, 1994, now Pat. No. 6,241,747, which is a continuation-in-part of application No. 08/055,989, filed on May 3, 1993, now abandoned.

(51) Int. Cl.
*A61B 17/08* (2006.01)
(52) U.S. Cl. ...................... 606/216; 606/213
(58) Field of Classification Search .......... 606/151, 606/153, 155, 213, 216, 217
See application file for complete search history.

(56) References Cited

U.S. PATENT DOCUMENTS

| 709,392 | A | 9/1902 | Brown |
|---|---|---|---|
| 733,723 | A | 7/1903 | Lukens |
| 789,401 | A | 5/1905 | Acheson |
| 816,026 | A | 3/1906 | Meier |
| 879,758 | A | 2/1908 | Foster |
| 1,142,510 | A | 6/1915 | Engle |
| 1,248,825 | A | 12/1917 | Dederer |
| 1,321,011 | A | 11/1919 | Cottes |
| 1,728,316 | A | 9/1929 | von Wachenfeldt |

(Continued)

FOREIGN PATENT DOCUMENTS

CN 2640420 9/2004

(Continued)

OTHER PUBLICATIONS

A. R. McKenzie, "An experimental multiple barbed suture for the long flexor tendons of the palm and fingers", The Journal of Bone and Joint Surgery, Aug. 1967, pp. 440-447, vol. 49B, No. 3.

(Continued)

*Primary Examiner*—Michael Peffley
(74) *Attorney, Agent, or Firm*—Angiotech

(57) ABSTRACT

A barbed bodily tissue connector for insertion into tissue comprises an elongated body having a substantially polygonal periphery in cross-section including at least three sides. Each side meets an adjacent side at an edge of the elongated body. A plurality of barbs project from the edges of the body. The barbs are configured such that they are yieldable in a direction toward the body and resist retraction from tissue in an opposite direction.

181 Claims, 3 Drawing Sheets

U.S. PATENT DOCUMENTS

| | | |
|---|---|---|
| 1,886,721 A | 11/1932 | O'Brien |
| 2,094,578 A | 10/1937 | Blumenthal et al. |
| 2,201,610 A | 5/1940 | Dawson, Jr. |
| 2,232,142 A | 2/1941 | Schumann |
| 2,254,620 A | 9/1941 | Miller |
| 2,355,907 A | 8/1944 | Cox |
| 2,421,193 A | 5/1947 | Gardner |
| 2,472,009 A | 5/1949 | Gardner |
| 2,572,936 A | 10/1951 | Kulp et al. |
| 2,684,070 A | 7/1954 | Kelsey |
| 2,779,083 A | 1/1957 | Eaton |
| 2,814,296 A | 11/1957 | Everett |
| 2,817,339 A | 12/1957 | Sullivan |
| 2,866,256 A | 12/1958 | Matlin |
| 2,910,067 A | 10/1959 | White |
| 2,988,028 A | 6/1961 | Alcamo |
| 3,003,155 A | 10/1961 | Mielzynski et al. |
| 3,068,869 A | 12/1962 | Shelden et al. |
| 3,068,870 A | 12/1962 | Levin |
| 3,123,077 A | 3/1964 | Alcamo |
| 3,166,072 A | 1/1965 | Sullivan, Jr. |
| 3,187,752 A | 6/1965 | Glick |
| 3,209,754 A | 10/1965 | Brown |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling et al. |
| 3,385,299 A | 5/1968 | Le Roy |
| 3,494,006 A | 2/1970 | Brumlik |
| 3,525,340 A | 8/1970 | Gilbert |
| 3,527,223 A | 9/1970 | Shein |
| 3,586,002 A | 6/1971 | Wood |
| 3,608,095 A | 9/1971 | Barry |
| 3,608,539 A | 9/1971 | Miller |
| 3,646,615 A | 3/1972 | Ness |
| 3,683,926 A | 8/1972 | Suzuki |
| 3,700,433 A | 10/1972 | Duhl |
| 3,716,058 A | 2/1973 | Tanner, Jr. |
| 3,720,055 A | 3/1973 | de Mestral et al. |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,918,455 A | 11/1975 | Coplan |
| 3,981,051 A | 9/1976 | Brumlik |
| 3,981,307 A | 9/1976 | Borysko |
| 4,006,747 A | 2/1977 | Kronenthal et al. |
| 4,043,344 A | 8/1977 | Landi et al. |
| 4,069,825 A | 1/1978 | Akiyama |
| 4,073,298 A | 2/1978 | Le Roy |
| 4,198,734 A | 4/1980 | Brumlik |
| 4,259,959 A | 4/1981 | Walker |
| 4,300,424 A | 11/1981 | Flinn et al. |
| 4,311,002 A | 1/1982 | Hoffmann et al. |
| 4,316,469 A | 2/1982 | Kapitanov |
| 4,317,451 A | 3/1982 | Cerwin et al. |
| 4,428,376 A | 1/1984 | Mericle |
| 4,430,998 A | 2/1984 | Harvey et al. |
| 4,434,796 A | 3/1984 | Karapetian et al. |
| 4,454,875 A | 6/1984 | Pratt et al. |
| 4,467,805 A | 8/1984 | Fukuda |
| 4,492,075 A | 1/1985 | Faure |
| 4,493,323 A | 1/1985 | Albright et al. |
| 4,505,274 A | 3/1985 | Speelman |
| 4,510,934 A | 4/1985 | Batra |
| 4,531,522 A | 7/1985 | Bedi et al. |
| 4,548,202 A | 10/1985 | Duncan |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards et al. |
| 4,676,245 A | 6/1987 | Fukuda |
| 4,719,917 A | 1/1988 | Barrows et al. |
| 4,776,337 A | 10/1988 | Palmaz |
| 4,832,025 A | 5/1989 | Coates |
| 4,841,960 A | 6/1989 | Garner |
| 4,873,976 A | 10/1989 | Schreiber |
| 4,887,601 A | 12/1989 | Richards |
| 4,895,148 A | 1/1990 | Bays et al. |
| 4,900,605 A | 2/1990 | Thorgersen et al. |
| 4,905,367 A | 3/1990 | Pinchuk et al. |
| 4,930,945 A | 6/1990 | Arai et al. |
| 4,948,444 A | 8/1990 | Schutz et al. |
| 4,950,285 A | 8/1990 | Wilk |
| 4,976,715 A | 12/1990 | Bays et al. |
| 4,981,149 A | 1/1991 | Yoon et al. |
| 4,994,073 A | 2/1991 | Green |
| 4,997,439 A | 3/1991 | Chen |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,047,047 A | 9/1991 | Yoon |
| 5,053,047 A | 10/1991 | Yoon |
| 5,084,063 A | 1/1992 | Korthoff |
| 5,102,418 A | 4/1992 | Granger et al. |
| 5,102,421 A | 4/1992 | Anspach, Jr. |
| 5,103,073 A | 4/1992 | Danilov et al. |
| 5,112,344 A | 5/1992 | Petros |
| 5,123,911 A | 6/1992 | Granger et al. |
| 5,123,913 A | 6/1992 | Wilk et al. |
| 5,123,919 A | 6/1992 | Sauter et al. |
| 5,127,413 A | 7/1992 | Ebert |
| 5,133,738 A | 7/1992 | Korthoff et al. |
| 5,141,520 A | 8/1992 | Goble et al. |
| 5,156,788 A | 10/1992 | Chesterfield et al. |
| 5,192,302 A | 3/1993 | Kensey et al. |
| 5,207,694 A | 5/1993 | Broome |
| 5,217,494 A | 6/1993 | Coggins et al. |
| 5,222,976 A | 6/1993 | Yoon |
| 5,224,946 A | 7/1993 | Hayhurst et al. |
| 5,246,441 A | 9/1993 | Ross et al. |
| 5,258,013 A | 11/1993 | Granger et al. |
| 5,269,783 A | 12/1993 | Sander |
| 5,292,326 A | 3/1994 | Green et al. |
| 5,320,629 A | 6/1994 | Noda et al. |
| 5,330,503 A | 7/1994 | Yoon |
| 5,341,922 A | 8/1994 | Cerwin et al. |
| 5,342,376 A | 8/1994 | Ruff |
| 5,352,515 A | 10/1994 | Jarrett et al. |
| 5,372,146 A | 12/1994 | Branch |
| 5,374,268 A | 12/1994 | Sander |
| 5,374,278 A | 12/1994 | Chesterfield et al. |
| 5,395,126 A | 3/1995 | Tresslar |
| 5,411,523 A | 5/1995 | Goble |
| 5,414,988 A | 5/1995 | DiPalma et al. |
| 5,425,746 A | 6/1995 | Proto et al. |
| 5,425,747 A | 6/1995 | Brotz |
| 5,450,860 A | 9/1995 | O'Connor |
| 5,500,000 A | 3/1996 | Feagin et al. |
| 5,500,991 A | 3/1996 | Demarest et al. |
| 5,520,691 A | 5/1996 | Branch |
| 5,533,982 A | 7/1996 | Rizk et al. |
| 5,536,582 A | 7/1996 | Prasad et al. |
| 5,546,957 A | 8/1996 | Heske |
| 5,584,859 A | 12/1996 | Brotz |
| 5,601,557 A | 2/1997 | Hayhurst |
| 5,683,417 A | 11/1997 | Cooper |
| 5,697,976 A | 12/1997 | Chesterfield et al. |
| 5,702,462 A | 12/1997 | Oberlander |
| 5,716,376 A | 2/1998 | Roby et al. |

| | | | |
|---|---|---|---|
| 5,722,991 A | 3/1998 | Colligan | |
| 5,887,594 A | 3/1999 | LoCicero, III | |
| 5,897,572 A | 4/1999 | Schulsinger et al. | |
| 5,931,855 A | 8/1999 | Buncke | |
| 5,964,783 A | 10/1999 | Grafton et al. | |
| 5,972,024 A | 10/1999 | Northrup, III et al. | |
| 5,984,933 A | 11/1999 | Yoon | |
| 6,012,216 A | 1/2000 | Esteves et al. | |
| 6,027,523 A | 2/2000 | Schmieding | |
| 6,056,778 A | 5/2000 | Grafton et al. | |
| 6,083,244 A | 7/2000 | Lubbers et al. | |
| 6,102,947 A | 8/2000 | Gordon | |
| 6,163,948 A | 12/2000 | Esteves et al. | |
| 6,241,747 B1 | 6/2001 | Ruff | |
| 6,251,143 B1 | 6/2001 | Schwartz et al. | |
| 6,270,517 B1 | 8/2001 | Brotz | |
| 6,443,962 B1 | 9/2002 | Gaber | |
| 6,478,809 B1 | 11/2002 | Brotz | |
| RE37,963 E | 1/2003 | Thal | |
| 6,599,310 B2 | 7/2003 | Leung et al. | |
| 6,645,226 B1 | 11/2003 | Jacobs et al. | |
| 6,773,450 B2 | 8/2004 | Leung et al. | |
| 6,848,152 B2 | 2/2005 | Genova et al. | |
| 6,905,484 B2 | 6/2005 | Buckman et al. | |
| 7,056,331 B2 | 6/2006 | Kaplan et al. | |
| 7,226,468 B2 | 6/2007 | Ruff | |
| 2003/0149447 A1 | 8/2003 | Morency et al. | |
| 2004/0060409 A1 | 4/2004 | Leung et al. | |
| 2004/0060410 A1 | 4/2004 | Leung et al. | |
| 2004/0088003 A1 | 5/2004 | Leung et al. | |
| 2004/0106949 A1 | 6/2004 | Cohn et al. | |
| 2004/0138683 A1 | 7/2004 | Shelton et al. | |
| 2004/0193191 A1 | 9/2004 | Starksen et al. | |
| 2005/0203576 A1 | 9/2005 | Sulamanidze et al. | |
| 2006/0079935 A1 | 4/2006 | Kolster | |
| 2006/0135994 A1 | 6/2006 | Ruff et al. | |
| 2006/0135995 A1 | 6/2006 | Ruff et al. | |
| 2007/0005109 A1 | 1/2007 | Popadiuk et al. | |
| 2007/0005110 A1 | 1/2007 | Collier et al. | |
| 2007/0038249 A1 | 2/2007 | Kolster | |
| 2007/0208355 A1 | 9/2007 | Ruff | |
| 2007/0224237 A1 | 9/2007 | Hwang et al. | |

FOREIGN PATENT DOCUMENTS

| | | |
|---|---|---|
| DE | 1810800 | 6/1970 |
| DE | 4302895 | 8/1994 |
| DE | 19618891 | 4/1997 |
| DE | 19833703 | 2/2000 |
| EP | 0428253 | 5/1991 |
| EP | 0576337 | 12/1993 |
| EP | 0612504 | 11/1997 |
| EP | 0826337 | 3/1998 |
| EP | 0839499 | 5/1998 |
| EP | 0913123 | 5/1999 |
| EP | 1075843 | 2/2001 |
| FR | 2619129 | 2/1989 |
| FR | 9208059 | 12/1993 |
| FR | 2693108 | 1/1994 |
| GB | 1091282 | 11/1967 |
| GB | 1428560 | 3/1976 |
| GB | 1506362 | 4/1978 |
| JP | 54116419 | 9/1979 |
| JP | 01113091 | 5/1989 |
| JP | 10085225 | 4/1998 |
| JP | 11332828 | 12/1999 |
| NZ | 501224 | 3/2002 |
| NZ | 531262 | 6/2002 |
| RU | 2139690 | 10/1999 |
| SU | 1745214 | 7/1992 |
| SU | 1752358 | 8/1992 |
| WO | 96/06565 | 3/1996 |
| WO | 98/52473 | 11/1998 |
| WO | 99/21488 | 5/1999 |
| WO | 00/51658 | 9/2000 |
| WO | 03/001979 | 1/2003 |
| WO | 03/017850 | 3/2003 |
| WO | 03/045255 | 6/2003 |
| WO | 03/103733 | 12/2003 |
| WO | 2004/014236 | 2/2004 |
| WO | 2004/030520 | 4/2004 |
| WO | 2004/030704 | 4/2004 |
| WO | 2004/030705 | 4/2004 |
| WO | 2006/061868 | 6/2006 |
| WO | 2007/133103 | 11/2007 |

OTHER PUBLICATIONS

M. A. Sulamanidze, T. G. Paikidze, & G. M. Sulamanidze, "Facial lifting with 'Aptos' threads", http://www.fonendo.com, Jul. 18, 2001, pp. 1-4.

Philip P. Dattilo Jr., Martin W. King, Nancy L. Cassill, & Jeffrey C. Leung, "Medical textiles: application of an absorbable barbed bi-directional surgical suture", Journal of Textile and Apparel, Technology and Management, Spring 2002, vol. 2, Issue 2.

CCPR Centro De Cirurgia Plastica E Reabilitacao, "Up Lifting (Aptos Threads)", http://www.ccpr.com.br/upl-I.htm, Aug. 19, 2002, pp. 1-2.

Hougtao Han, Lee E. Weiss, & Michael L. Reed, "Mating and piercing micromechanical structures for surface bonding applications", Micro Electric Mechanical Systems (MEMS-91), Jan. 31-Feb. 2, 1991, Nara, Japan, CH2597-9/91, pp. 253-258.

H. J. Buncke Jr. & W. P. Schulz, "The suture repair of one-millimeter vessels", Micro-vascular Surgery, Report of First Conference, Oct. 6-7, 1966, pp. 24-35 (note p. 34).

M. A. Sulamanidze, P. F. Fournier, T. G. Paikidze, & G. M. Sulamanidze, "Removal of facial soft tissue ptosis with special threads", Dermatologic Surgery, May 2002, pp. 367-371, vol. 28.

Gregory L. Ruff, "Declaration of Dr. Gregory L. Ruff", Aug. 19, 2005.

M. A. Sulamanidze, M. A. Shiffman, T. G. Paikidze, G. M. Sulamanidze, & L. G. Gavashell, "Facial lifting with Aptos threads", International Journal of Cosmetic Surgery and Aesthetic Dermatology, 2001, pp. 1-8, No. 4.

G. M. Semenov, V. L. Petrishin, & M. V. Kovshova, "Surgical suture", 2001, Piter, Saint Petersburg, pp. 12-13 and 92-98.

U. W. Boenisch, K. J. Faber, M. Ciarelli, J. R. Steadman, & S. P. Arnoczky, "Pull-out strength and stiffness of meniscal repair using absorbable arrows or Ti-Cron vertical and horizontal loop sutures", American Journal of Sports Medicine, Sep.-Oct. 1999, pp. 626-631, vol. 27, Issue 5.

Philip P. Dattilo Jr., Martin W. King, & Jeffrey C. Leung, "Tissue holding performance of knotless absorbable sutures", Society for Biomaterials 29th Annual Meeting Transactions, 2003, p. 101.

Quill Medical, Inc.; EP 07015905.8; Extended European Search Report dated Oct. 23, 2007.

G. Ruff, U.S. Appl. No. 11/968,496, filed Jan. 2, 2008.

G. Ruff, U.S. Appl. No. 11/968,494, filed Jan. 2, 2008.

BARBED TISSUE CONNECTOR

CROSS-REFERENCES TO RELATED APPLICATIONS

This application is a continuation application of U.S. patent application Ser. No. 11/747,085, filed on May 10, 2007, currently pending, which is a continuation application of U.S. patent application Ser. No. 10/420,119, filed on Apr. 21, 2003, now U.S. Pat. No. 7,226,468, which is a continuation application of U.S. patent application Ser. No. 09/629,428, filed on Jul. 31, 2000, now abandoned, which is a continuation application of U.S. patent application Ser. No. 08/324,529, filed on Oct. 18, 1994, now U.S. Pat. No. 6,241,747, which is a continuation-in-part application of U.S. patent application Ser. No. 08/055,989, filed on May 3, 1993, now abandoned.

BACKGROUND OF THE INVENTION

This invention relates to a barbed tissue connector, and more particularly, to such a connector which can be used to quickly and effectively close a body wound.

Human wounds are typically repaired with a filament introduced into the tissue by a needle attached to one end. After piercing the opposing faces of the wound, the needle is removed, and the ends of the suture are tied together with at least three overhand knots. Such a technique requires considerable time and expertise on the part of the surgeon. There are also a number of other drawbacks to repairing a wound in this manner. For example, it is very difficult to use sutures to repair wounds where there is insufficient space to properly manipulate the suture, especially those wounds repaired using fiber optic visualization. The suture forms a loop as it is tied, and this loop constricts blood flow to the tissue in its confines, promoting necrosis of the wound margins. Further, if the needle's passage was noncircular, the tissue will be distorted as it is secured by the suture.

Alternatives to conventional sutures are known in the prior art. Staples, as shown, for example, in U.S. Pat. No. 4,994,073, to Green, are often used for approximating the superficial layer of the wound. Staples, however, are generally unsuitable for deeper layers of tissue.

The patent to Alcamo, U.S. Pat. No. 3,123,077, discloses a roughened suture which can be passed through tissue in one direction, but resists movement in the opposite direction. The Alcamo suture, however, still must be sewn, as by a conventional technique, and the trailing end must be secured with knots. Thus, although there is less slippage of the suture in the wound, most of the disadvantages of sutures noted above are also found in the Alcamo suture.

The patent to Tanner, U.S. Pat. No. 3,716,058, discloses a relatively rigid suture with one or more barbs on opposite ends of an arcuate body. One disadvantage of the Tanner suture is that the rigid barbs, which protrude from the suture as it is inserted, will lacerate tissue and prevent retrograde repositioning. Further, since the barbs are only placed at the ends of the suture, the forces applied to the tissue by the barbs will be limited to a relatively small area; this substantially increases the pressure on the blood vessels ensnared by a barb and severely restricts blood flow to the area.

It will be seen from the foregoing that there is a need for a tissue connector which can be placed more expeditiously than sutures, is self-retaining, obviates distortion of the tissue, can close tissue inaccessible to conventional procedures, and which preserves blood flow by broadly distributing the retention force.

SUMMARY OF THE INVENTION

It is an object of the present invention to overcome the aforementioned problems in the prior art and to provide an improved tissue connector.

In accordance with the present invention there is provided a barbed tissue connector comprising: an elongated body having a point formed on one end, the body being formed of a material sufficiently hard for the point to pierce tissue and enable the connector to be inserted in tissue when a substantially axial force is applied to the body; and a plurality of barbs projecting from the body, the barbs being disposed around the periphery of the body along a length of the body which extends from adjacent the one end to a predetermined location on the body, the barbs being configured such that they are yieldable in a direction toward the body and are generally rigid in an opposite direction, and the barbs being sufficiently resilient to return to a predetermined position after deflection therefrom.

In one embodiment of the present invention, the barbed tissue connector includes an elongated body and a plurality of barbs which are disposed in a helical pattern on the body and extend from a pointed end of the connector to a predetermined location on the body. Each barb includes a first side, which forms an obtuse angle with the body, and a second side which forms an acute angle with the body. The body is substantially rigid and sufficiently resilient to return to a predetermined position after deflection therefrom. When the connector is inserted in tissue to repair a wound, the pointed end pierces tissue and the barbs yield toward the body to facilitate entry of the connector.

When the connector has been placed in a desired position in tissue, the barbs strongly resist movement away from this position. The connector can be inserted by gripping the connector in the hand and pushing the connector into the tissue, or the connector can be inserted by means of an inserting device which is withdrawn when the connector is in place.

A principal advantage of the barbed tissue connector of the present invention is that it permits a surgeon to rapidly and securely attach the edges of a wound in human tissue without the necessity for threading and tying numerous individual stitches or for the use of a complicated or elaborate tool to insert the connector. The connector is configured to minimize damage to tissue when inserted and to minimize scarring or tissue necrosis across the wound. The connector is capable of insertion into the faces of a wound, can connect tissue at the bottom of a deep wound, and can connect tissue which is inaccessible to a staple. Finally, the connector of the present invention can be inserted quickly and accurately by a surgeon who only has access to tissue from a small opening or from only one direction, as, for example, during an endoscopic procedure.

Other features and advantages will become apparent upon reference to the following description of the preferred embodiment when read in light of the attached drawings.

DESCRIPTION OF THE PREFERRED EMBODIMENTS

The present invention allows a surgeon to rapidly and securely attach the edges of a wound in human tissue without the necessity for threading and tying numerous individual stitches or for using a complicated or elaborate tool. As used herein, the term "wound" means an incision, laceration, cut, or other condition where suturing, stapling, or the use of another tissue connecting device might be required.

Figure 1:
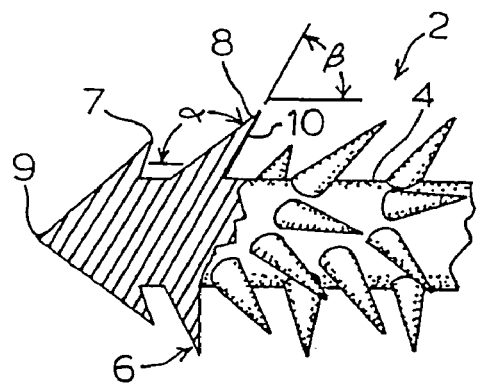
FIG. 1 is a side view of the connector of the present invention, with a section broken away to more clearly show the arrangement of the barbs.
Figure 2:
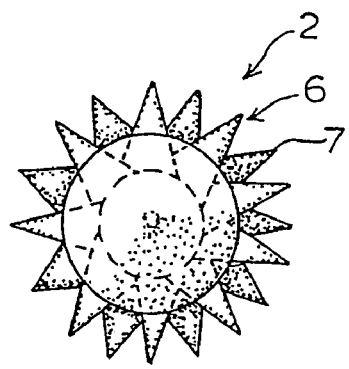
FIG. 2 is an end view of the connector shown in FIG. 1.

With reference to FIGS. 1 and 2, there is shown a barbed tissue connector 2 constructed in accordance with the present invention. Connector 2 includes a body 4 which is generally circular in cross section and a plurality of closely-spaced barbs 6 which extend around the periphery of the body 4. A pointed end 9 is formed on the body 4 to facilitate penetration of the connector 2 into tissue. The body 4 preferably has sufficient dimensional stability to assume a substantially rigid configuration during use and is sufficiently resilient to return to a predetermined shape after deflection therefrom. In some applications, it may be desirable for the body 4 to be flexible and substantially nonresilient so that the shape of an inserted connector will be determined by surrounding tissue.

Barbs 6 serve to hold the connector in tissue and resist retraction of the connector from the tissue. The barbs 6 can be arranged in any suitable pattern, for example, in a helical pattern as shown in FIG. 1. In a helical pattern of barbs 6, it is preferable that the number of barbs occupying one revolution not be an integer, thereby avoiding parallel axial rows of barbs; such an arrangement provides a more uniform distribution of forces on the tissue and lessens the tendency of an inserted connector 2 to cut through tissue. If the number of barbs in one revolution is not an integer, the barbs in successive revolutions will be offset, as shown in FIG. 2, and the amount of offset will determine which barbs are in axial alignment. For example, if the barbs in successive revolutions are offset by ½ barb, the barbs in every second revolution will be in axial alignment, and by extension, if the barbs in each successive revolution are offset by 1/x barb, the barbs in every x revolution will be in axial alignment.

As shown in FIG. 1, each barb 6 includes a first side 8 which forms an obtuse angle alpha with the body 4 and a second side 10 which forms an acute angle beta with the body 4. Each barb 6 tapers to a point 7, and the amount of difference between the angle alpha of side 8 and angle beta of side 10 will control the amount of taper in the barb 6. A barb 6 which tapers from a broad base to a narrow tip can be effective in resisting retraction, yet will yield toward the body 4 during insertion to reduce the effort and tissue damage associated with insertion of the connector 2. The barbs 6 can be generally conical, as shown in FIG. 1, or they can be any other shape which will function in substantially the same manner as the conical barbs.

The configuration of barbs 6 and the surface area of the barbs can vary depending upon the tissue in which the connector 2 is used. The proportions of the barbs 6 can remain relatively constant while the overall length of the barbs and the spacing of the barbs are determined by the tissue being connected. For example, if the connector 2 is intended to be used to connect the edges of a wound in skin or tendon, each barb 6 can be made relatively short to facilitate entry into this rather firm tissue. If the connector 2 is intended for use in fatty tissue, which is relatively soft, the barbs can be made longer and spaced farther apart to increase the holding ability in the soft tissue. As shown in FIG. 1, the barbs 6 on connector 2 have a uniform unidirectional configuration, that is, the barbs 6 are uniformly spaced on body 4 and all the sides 8 are oriented in the same direction, facing pointed end 9. Connector 2 can be inserted into tissue with the sides 8 of each barb 6 facing in the direction of motion. Connector 2 will prevent movement of tissue in the direction in which it was inserted. A pair of connectors 2 inserted adjacent to each other and in opposite directions will prevent movement of tissue in either direction across a wound.

Connector 2 can be formed of a material sufficiently hard for point 9 to pierce tissue and enable the connector to be inserted in tissue when a substantially axial force is applied to body 4. Connector 2 is preferably composed of a bioabsorbable compound, such as a polyglycolic acid or polylactic acid polymer or copolymer. The use of a bioabsorbable material eliminates the necessity of removing the connector from the patient, which can be a painful and possibly dangerous process. Connector 2 can be formed, for example, by injection molding.

In one representative example of connector 2 for use in muscular tissue, the body 4 is formed from polyglycolic acid, has a length of 1 to 5 cm, and a diameter of about 1 mm. The diameter of a circle extending around points 7 of barbs 6 will be about 3 mm, and the barbs are spaced apart from each other on body 4 by a distance of 1 mm. Side 8 forms an angle of 135 degrees with the body 4 and side 10 forms an angle of 75 degrees with the body 4.

Figure 3:
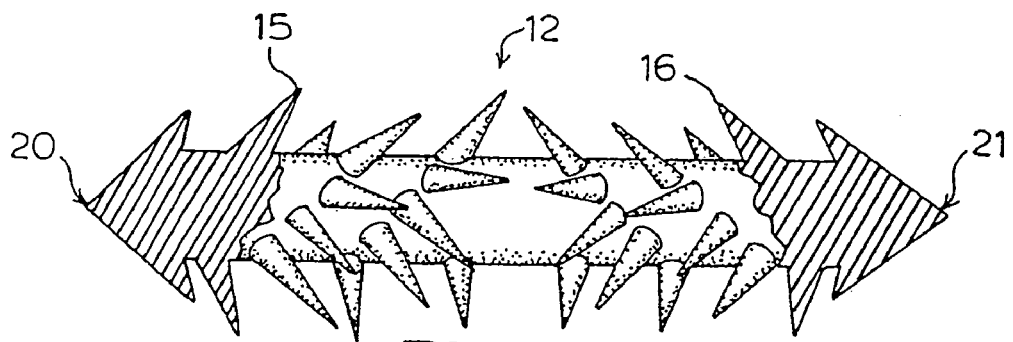
FIG. 3 is a side view of another embodiment of the present invention, with a section of a connector broken away.

In FIG. 3, there is shown a second embodiment of the present invention in which barbs 16 are arranged in a uniform bidirectional configuration on a barbed tissue connector 12. Barbs 16 are constructed in the same manner as barbs 6 on connector 2. A first set of barbs 15 on connector 12 are arranged in a helical pattern and face a pointed end 20, and a second set of barbs 16 on connector 12 are arranged in a helical pattern and face a pointed end 21. Each of the pointed ends 20, 21 should be sufficiently hard and sharp to easily penetrate tissue in which the connector is to be used. Connector 12 is particularly suitable for applications where the edges of a wound are prone to separate. Connector 12 can be used by inserting one of the ends, for example end 20, into a first side of a wound (not shown), spreading the wound slightly to expose the second side of the wound, inserting the end 21 of the connector 12 into the second side of the wound, and then pressing the edges of the wound together. The barbs 15 and 16 on the ends of the connector 12 will grasp the tissue on each side of the wound and prevent the edges of the wound from spreading.

Figure 4:
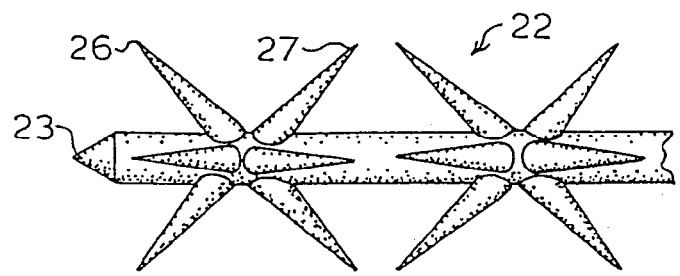
FIG. 4 is a side view of another embodiment of the present invention.

With reference to FIG. 4, there is shown another embodiment of the present invention in which a barbed tissue connector 22 has a nonuniform bidirectional configuration. Connector 22 comprises a pointed end 23 and one or more barbs 26 facing a first direction which alternate with one or more barbs 27 facing a second direction. At each axial location, there can be a number, e.g. 4-9, of circumferentially-spaced barbs 26 or 27. To insert connector 22 into tissue, the surgeon would use an inserting device 80 as described below. The arrangement of barbs 26, 27 on connector 22 would prevent any localized movement of tissue relative to the connector in an axial direction.

Figure 5:
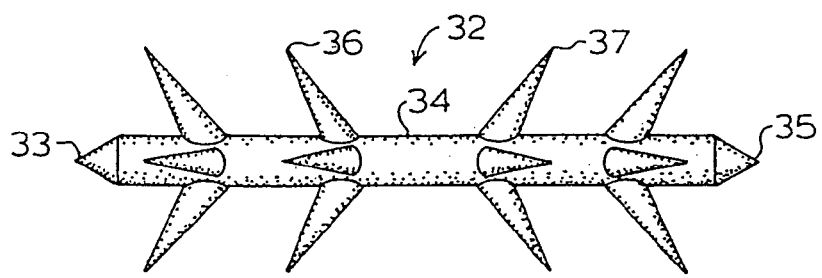
FIG. 5 is a side view of another embodiment of the present invention.

With reference to FIG. 5, there is shown another embodiment of the present invention in which a barbed tissue connector 32 has a uniform bidirectional configuration. Connector 32 comprises a body 34 having pointed ends 33 and 35. A plurality of axially-spaced barbs 36 adjacent pointed end 33 face toward end 35, and a plurality of axially-spaced barbs 37 adjacent pointed end 35 face toward end 33. Barbs 36 and 37 can be circumferentially-spaced around body 34 at each axial location, or the barbs 36 and 37 can be of the same construction and arranged in the same pattern as barbs 6 on connector 2. To insert a connector 32, the surgeon would use an inserting device 80 as described below. If the body 34 of the connector 32 is sufficiently rigid, the connector 32 would prevent tissue retained by the barbs 36 from moving toward end 35 and tissue retained by barbs 37 from moving toward end 33. It will be apparent that only one end of connector 32 needs to be pointed; two pointed ends are preferable, however, so that the surgeon does not have to take the time to insure that connector 32 is oriented in the inserting device 80 with a pointed end protruding from the inserting device.

Figure 6:
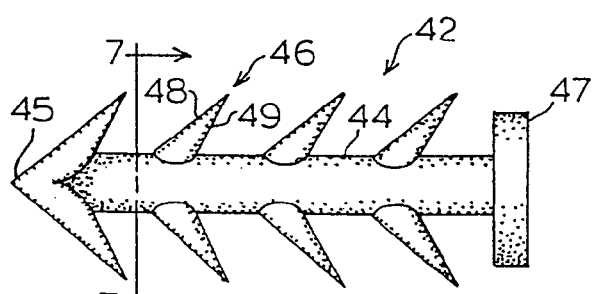
FIG. 6 is a side view of another embodiment of the present invention.
Figure 7:
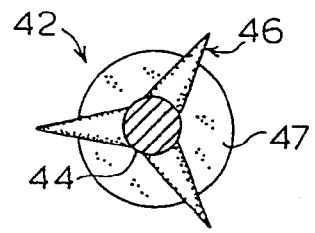
FIG. 7 is a sectional view taken along the line 7-7 in FIG. 6.

With reference to FIGS. 6 and 7, there is shown another embodiment of the present invention in which a barbed tissue connector 42 comprises a body 44 having a pointed end 45 for penetration into tissue. A head 47 is formed on an opposite end of body 44. A plurality of circumferentially-spaced barbs 46 are formed on body 44 at each of a number of axial locations. As shown in FIG. 7, three barbs 46 are formed at each axial location; however, more or less than three barbs 46 could be used for certain applications. Barbs 46 include a first side 48 formed at an obtuse angle to the body 44 and a second side 49 which projects from body 44 at an acute angle. The connector 42 can be forced into tissue by applying a force to the head 47. The connector 42 can be applied by hand, or it can be inserted using an inserting device 80 as described below.

The connector 42 can be formed entirely of a bioabsorbable material, or the head 47 and the body 44 can be composed of different materials. For example, the body 44 can be composed of a bioabsorbable material, and the head 47 can be composed of metal for superior strength and to facilitate insertion of the connector 42. Head 47 can be made flat, as shown in FIG. 6, or the head can be formed by a single ring of barbs (not shown) facing in a direction opposite to that of the barbs 46.

In use, a series of connectors 42 can be inserted into tissue, such as along the edges and in the field of a skin graft. After an adequate amount of time has passed for the wound to heal, the tissue beneath each head 47 could be depressed slightly to permit the head 47 to be cut from the body 44. The tissue would then rise up over the cut end of the body. Such a process would reduce scarring which could result from a long-term projection of the body 44 through tissue and would eliminate the necessity to remove connectors 42 from the patient.

Figure 8:
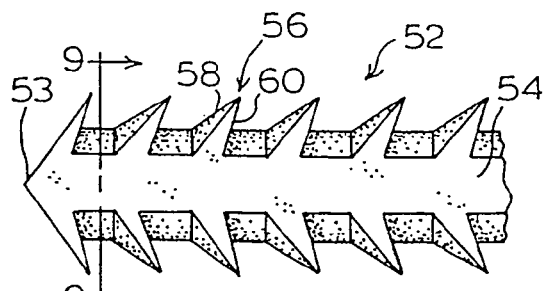
FIG. 8 is a side view of another embodiment of the present invention.
Figure 9:
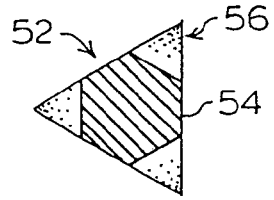
FIG. 9 is a sectional view taken along the line 9-9 in FIG. 8.

With reference to FIGS. 8 and 9, there is shown another embodiment of the present invention in which a barbed tissue connector 52 has a uniform unidirectional configuration. Connector 52 comprises a body 54 having a non-circular cross-sectional shape. Body 54 includes a plurality of barbs 56 which are generally triangular in cross section and are equally spaced around the periphery of the body at a series of axial locations. Each of the barbs 56 includes a first side 58 disposed at an obtuse angle to body 54 and a second side 60 disposed at an acute angle to the body. Body 54 includes a pointed end 53 to facilitate entry in tissue. Use of a non-circular cross-sectional shape increases the surface area of the connector 52 and facilitates the formation of the multiple barbs on the connector. For example, barbs 56 can be formed on a piece of stock having a triangular cross section by removing material at successive axial locations from the three edges of the stock. It will be apparent that a similar process could be used to form barbs on stock of a different cross section (not shown), for example, a rectangular or hexagonal cross section.

Figure 10:
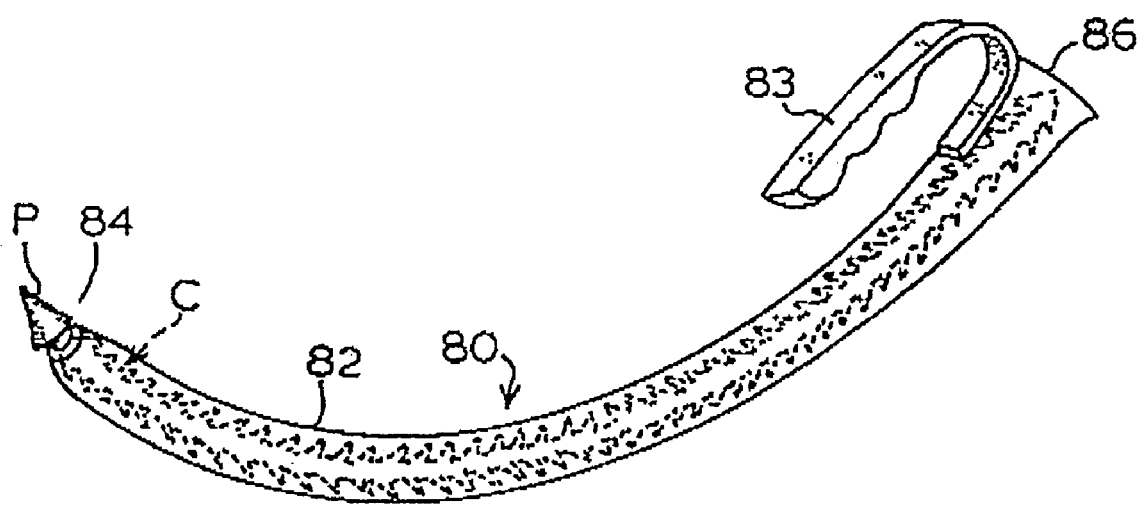
FIG. 10 is a perspective view of an inserting device for use with a barbed tissue connector of the present invention.
Figure 11:
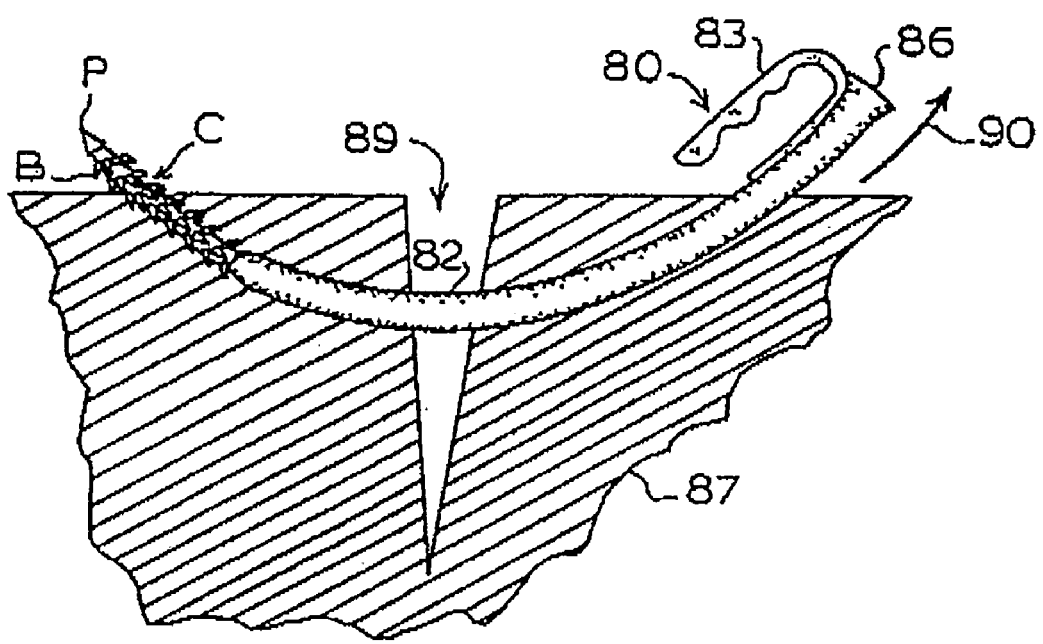
FIG. 11 is a view showing the inserting device and connector in a wound.

In the use of the disclosed connectors, such as connectors 2 and 42, the surgeon can grip the connector in one hand and push the connector into the tissue. As an alternative to directly inserting the connectors into the tissue, the surgeon can use an inserting device 80 as shown in FIGS. 10 and 11. The inserting device 80 comprises a circular tubular body 82. The tubular body 82 can be generally arcuate in an axial direction, and the body 82 is sufficiently long to contain at least a portion of a barbed tissue connector C. Device 80 has an inwardly tapered leading end 84 and an outwardly tapered, or flared, trailing end 86. A handle 83 is provided on body 82 adjacent trailing end 86 to enable the surgeon to manipulate the inserting device 80.

In order to facilitate entry of the connector C and the device 80 into tissue, a connector C is positioned in tubular body 82 with a pointed end P of the connector C extending from leading end 84. In a preferred embodiment, the interior diameter of the body 82 is made slightly smaller than the outside diameter of the connector C so that the barbs B of a connector C in the body 82 will press against the body 82; as a result, the connector C will be retained in the body 82 during insertion in tissue with the point P properly positioned outside of the body 82. The connector can also be positioned in body 82 with a barb B outside of body 82 to insure that the connector C will not be pushed back in the body 82 during insertion. In one application of device 80, the surgeon inserts the body 82 having connector C therein into the patient's tissue 87 until the connector C reaches a desired position, for example, the position shown in FIG. 11. Device 80 is then withdrawn in the direction of arrow 90, and a barb, or barbs, B on the connector C penetrates and catches the tissue 87 to hold the connector C in the inserted position.

Use of the inserting device 80 is particularly recommended when the connector C includes multiple barbs facing more than one direction, such as connectors 22 and 32, or when the connector is too flexible for insertion without additional support.

While the present invention has been described with respect to certain preferred embodiments thereof, it is to be understood that numerous variations in the details of construction, the arrangement and combination of parts, and the type of materials used may be made without departing from the spirit and scope of the invention.

I claim:

1. A barbed bodily tissue connector for insertion into tissue comprising:
   an elongated body having a first end, a second end, a substantially polygonal periphery in cross-section including at least three sides, each side meeting an adjacent side at an edge of the elongated body; and
   a plurality of barbs, each barb projecting from one of the edges of the body, wherein a first portion of the barbs extend along a first portion of the body and are oriented in one direction, the barbs being configured such that they are yieldable in a direction toward the body and resist retraction from tissue in an opposite direction.

2. The barbed bodily tissue connector of claim 1, wherein one of the first end and the second end comprises an end adapted to penetrate the tissue for facilitating entry of the connector into the tissue.

3. The barbed bodily tissue connector of claim 2, wherein the adapted end comprises a pointed end formed of a material sufficiently hard for the pointed end to pierce tissue and to enable the connector to be inserted in tissue when a substantially axial force is applied to the body of the connector.

4. The barbed bodily tissue connector of claim 3, wherein the body of the connector is formed of a material sufficiently hard for the pointed end to pierce tissue and to enable the connector to be inserted in tissue when a substantially axial force is applied to the body of the connector.

5. The barbed bodily tissue connector of claim 3, wherein the pointed end of the connector is free of barbs.

6. The barbed bodily tissue connector of claim 1, wherein the connector comprises a bioabsorbable material.

7. The barbed bodily tissue connector of claim 6, wherein the bioabsorbable material comprises polyglycolic acid polymer, polyglycolic acid copolymer, polylactic acid polymer, or polylactic acid copolymer.

8. The barbed bodily tissue connector of claim 1, wherein certain adjacent barbs face toward each other.

9. The barbed bodily tissue connector of claim 1, wherein one of the first and second ends comprises a head end.

10. The barbed bodily tissue connector of claim 1, wherein the body has sufficient dimensional stability to assume a substantially rigid configuration during use thereof.

11. The barbed bodily tissue connector of claim 1, wherein the body is sufficiently resilient to return to a predetermined shape after deflection therefrom.

12. The barbed bodily tissue connector of claim 1, wherein the body is flexible and substantially nonresilient whereby the shape of an inserted connector will be determined by the surrounding tissue.

13. The barbed bodily tissue connector of claim 1, wherein the periphery in cross-section is one of triangular, rectangular, or hexagonal.

14. A barbed bodily tissue connector for insertion into tissue comprising:
an elongated body having a first end, a second end, a substantially polygonal periphery in cross-section including at least three sides, each side meeting an adjacent side at an edge of the elongated body; and
a plurality of barbs, each barb projecting from one of the edges of the body, wherein a first portion of the barbs extend along a first portion of the body and are oriented in one direction, and wherein a second portion of the barbs extend along a second portion of the body and are oriented in an opposite direction to the first portion of the barbs, the barbs being configured such that they are yieldable in a direction toward the body and resist retraction from tissue in an opposite direction.

15. The barbed bodily tissue connector of claim 14, wherein one of the first end and the second end comprises an end adapted to penetrate the tissue for facilitating entry of the connector into the tissue.

16. The barbed bodily tissue connector of claim 15, wherein the adapted end comprises a pointed end formed of a material sufficiently hard for the pointed end to pierce tissue and to enable the connector to be inserted in tissue when a substantially axial force is applied to the body of the connector.

17. The barbed bodily tissue connector of claim 16, wherein the body of the connector is formed of a material sufficiently hard for the pointed end to pierce tissue and to enable the connector to be inserted in tissue when a substantially axial force is applied to the body of the connector.

18. The barbed bodily tissue connector of claim 16, wherein the pointed end of the connector is free of barbs.

19. The barbed bodily tissue connector of claim 14, wherein the connector comprises a bioabsorbable material.

20. The barbed bodily tissue connector of claim 19, wherein the bioabsorbable material comprises polyglycolic acid polymer, polyglycolic acid copolymer, polylactic acid polymer, or polylactic acid copolymer.

21. The barbed bodily tissue connector of claim 14, wherein certain adjacent barbs face toward each other.

22. The barbed bodily tissue connector of claim 14, wherein one of the first and second ends comprises a head end.

23. The barbed bodily tissue connector of claim 14, wherein the body has sufficient dimensional stability to assume a substantially rigid configuration during use thereof.

24. The barbed bodily tissue connector of claim 14, wherein the body is sufficiently resilient to return to a predetermined shape after deflection therefrom.

25. The barbed bodily tissue connector of claim 14, wherein the body is flexible and substantially nonresilient whereby the shape of an inserted connector will be determined by the surrounding tissue.

26. The barbed bodily tissue connector of claim 14, wherein
the barbs along a length of the body extending from adjacent the first end to a first axial location on the body face the first end;
the barbs along a length of the body extending from adjacent the second end to a second axial location face the second end; and
the length from adjacent the second end to the second axial location is less than the distance from the second end to the first axial location.

27. The barbed bodily tissue connector of claim 14, wherein
the barbs along a length of the body extending from adjacent the first end to a first axial location on the body face the second end;
the barbs along a length of the body extending from adjacent the second end to a second axial location face the first end; and
the length from adjacent the second end to the second axial location is less than the distance from the second end to the first axial location.

28. The barbed bodily tissue connector of claim 14, wherein the periphery in cross-section is one of triangular, rectangular, or hexagonal.

29. A method for bringing together one side and an other side of an open wound in tissue with a barbed tissue connector, where the barbed tissue connector has an elongated body, a pointed end, and a substantially polygonal periphery in cross-section including at least three sides, each side meeting an adjacent side at an edge of the elongated body, and a plurality of barbs, each barb projecting from one of the edges of the body, the barbs being sized and shaped to resist retraction of the barbed tissue connector from the tissue,
said method comprising:
(i) inserting the barbed tissue connector via the pointed end into tissue from one side of the wound,
(ii) penetrating through tissue on the one side of the wound, and (iii) penetrating into tissue at the other side of the wound such that a portion of the body extends from the tissue at the one side of the wound.

30. The method of claim 29, said method comprising:
(iv) inserting another barbed tissue connector, where the other barbed tissue connector has an elongated body, a pointed end, a substantially polygonal periphery in cross-section including at least three sides, each side meeting an adjacent side at an edge of the elongated body, and a plurality of barbs, each barb projecting from one of the edges of the body, the barbs of the other barbed tissue connector being sized and shaped to resist retraction of the other barbed tissue connector from the tissue, via the pointed end of the other barbed tissue connector from the other side of the wound,
(v) penetrating through tissue at the other side of the wound, and
(vi) penetrating into tissue at the one side of the wound.

31. The method of claim 29, wherein inserting the barbed tissue connector is accomplished with an inserting device.

32. The method of claim 31, wherein the inserting device comprises a tubular body.

33. The method of claim 29, wherein the barbed tissue connector comprises a bioabsorbable material.

34. The method of claim 33, wherein the bioabsorbable material comprises polyglycolic acid polymer, polyglycolic acid copolymer, polylactic acid polymer, or polylactic acid copolymer.

35. The method of claim 29, wherein the pointed end is free of barbs.

36. A surgical method for bringing together two tissue portions on either side of a tissue separation in tissue with a barbed tissue connector, where the barbed tissue connector has an elongated body, a first pointed end, a second pointed end, a length, and a substantially polygonal periphery in cross-section including at least three sides, each side meeting an adjacent side at an edge of the elongated body, and a plurality of barbs, each barb projecting from one of the edges of the body, the barbs being sized and shaped to resist retraction of the barbed tissue connector from the tissue, the barbed tissue connector having the barbs oriented in one direction for a first portion of the length of the body and in an opposite direction for a second portion of the length of the body, said method comprising:
(a) at the tissue separation, inserting the barbed tissue connector via the first pointed end into tissue at a position on one side of the tissue separation;
(b) repeating step (a) at the other side of the tissue separation, using the second pointed end of the barbed tissue connector, at a position located across the tissue separation from the position in which the first pointed end of the barbed tissue connector was inserted; and
(c) bringing the two tissue portions together.

37. The surgical method of claim 36, wherein bringing the two tissue portions together in step (c) is accomplished by pressing the two tissue portions together.

38. The surgical method of claim 36, wherein bringing the two tissue portions together in step (c) is accomplished by pushing the barbed tissue connector through the tissue.

39. The method of claim 36, wherein inserting the barbed tissue connector is accomplished with an inserting device.

40. The method of claim 39, wherein the inserting device comprises a tubular body.

41. The surgical method of claim 36, wherein the two tissue portions comprise two sides of an open wound in skin.

42. The surgical method of claim 36, wherein the barbed tissue connector comprises a bioabsorbable material.

43. The surgical method of claim 42, wherein the bioabsorbable material comprises polyglycolic acid polymer, polyglycolic acid copolymer, polylactic acid polymer, or polylactic acid copolymer.

44. The surgical method of claim 36, wherein the two tissue portions comprise portions of a tendon.

45. The surgical method of claim 36, wherein:
(a) the two tissue portions comprise two sides of an open wound at the skin of a patient, and
(b) the first pointed end and the second pointed end are free of barbs.

46. A surgical method for bringing together two tissue portions on either side of a tissue separation in tissue with a barbed tissue connector, where the barbed tissue connector has an elongated body, a pointed end, a length, and a substantially polygonal periphery in cross-section including at least three sides, each side meeting an adjacent side at an edge of the elongated body, and a plurality of barbs, each barb projecting from one of the edges of the body, the barbs being sized and shaped to resist retraction of the barbed tissue connector from the tissue and permitting movement of the barbed tissue connector through the tissue in the direction the barbed tissue connector is inserted, said method comprising:
(a) at the tissue separation, inserting the barbed tissue connector, via the pointed end, into tissue at one side of the tissue separation,
(b) penetrating through tissue on the one side of the separation, and
(c) penetrating into tissue on the other side of the separation wound such that a portion of the body extends from the tissue at the one side of the tissue separation.

47. The method of claim 46, said method comprising:
(d) inserting another barbed tissue connector, where the other barbed tissue connector has an elongated body, a pointed end, a length, and a substantially polygonal periphery in cross-section including at least three sides, each side meeting an adjacent side at an edge of the elongated body, and a plurality of barbs, each barb projecting from one of the edges of the body, the barbs being sized and shaped to resist retraction of the barbed tissue connector from the tissue and permitting movement of the barbed tissue connector through the tissue in the direction the barbed tissue connector is inserted, via the pointed end of the other barbed tissue connector from the other side of the tissue separation,
(e) penetrating through tissue on the other side of the of the separation, and
(f) penetrating into tissue on the one side of the separation.

48. The surgical method of claim 46, wherein the two tissue portions comprise sections of a tendon.

49. The surgical method of claim 46, wherein the two tissue portions comprise two sides of an open wound in skin.

50. The surgical method of claim 46, wherein the barbed tissue connector comprises a bioabsorbable material.

51. The surgical method of claim 50, wherein the bioabsorbable material comprises polyglycolic acid polymer, polyglycolic acid copolymer, polylactic acid polymer, or polylactic acid copolymer.

52. A method for inserting a barbed tissue connector into tissue, where the barbed tissue connector has an elongated body, a pointed end, an opposite end, and a substantially polygonal periphery in cross-section including at least three sides, each side meeting an adjacent side at an edge of the elongated body, and a plurality of barbs, each barb projecting from one of the edges of the body, the barbs being sized and shaped to resist retraction of the barbed tissue connector from the tissue, said method comprising inserting the pointed end into tissue by applying force to the opposite end such that a portion of the body extends from the tissue.

53. The method of claim 52, wherein the opposite end comprises a head end.

54. The method of claim 53, wherein after an adequate amount of time has passed for healing, depressing the tissue beneath the head end and cutting the head end from the elongated body, permitting the tissue to rise up over the cut end of the elongated body.

55. The method of claim 52, wherein inserting the barbed tissue connector is accomplished with an inserting device.

56. The method of claim 55, wherein the inserting device comprises a tubular body.

57. The surgical method of claim 52, wherein the barbed tissue connector comprises a bioabsorbable material.

58. The surgical method of claim 57, wherein the bioabsorbable material comprises polyglycolic acid polymer, polyglycolic acid copolymer, polylactic acid polymer, or polylactic acid copolymer.

59. A method for bringing together one side and an other side of an open wound in tissue with a barbed tissue connector, where the barbed tissue connector has an elongated body, a pointed end, and a substantially polygonal periphery in cross-section including at least three sides, each side meeting an adjacent side at an edge of the elongated body, and a plurality of barbs, each barb projecting from one of the edges of the body, the barbs being sized and shaped to resist retraction of the barbed tissue connector from the tissue, said method comprising:
   (i) inserting the barbed tissue connector via the pointed end into tissue from one side of the wound,
   (ii) penetrating through tissue on the one side of the wound,
   (iii) penetrating into tissue at the other side of the wound such that a portion of the body extends from the tissue at the one side of the wound,
   (iv) inserting another barbed tissue connector, where the other barbed tissue connector has an elongated body, a pointed end, a periphery, and a plurality of closely spaced barbs which extend around the periphery of the body, the barbs of the other barbed tissue connector being sized and shaped to resist retraction of the other barbed tissue connector from the tissue, via the pointed end of the other barbed tissue connector from the other side of the wound,
   (v) penetrating through tissue at the other side of the wound, and
   (vi) penetrating into tissue at the one side of the wound such that a portion of the body of the another barbed tissue connector extends from the tissue at the other side of the wound.

60. A surgical method for bringing together two tissue portions on either side of a tissue separation in tissue with a barbed tissue connector, where the barbed tissue connector has an elongated body, a first pointed end, a second pointed end, and a substantially polygonal periphery in cross-section including at least three sides, each side meeting an adjacent side at an edge of the elongated body, and a plurality of barbs, each barb projecting from one of the edges of the body, the barbs being sized and shaped to resist retraction of the barbed tissue connector from the tissue, the barbed tissue connector having the barbs oriented in one direction for a first portion of the length of the body and in an opposite direction for a second portion of the length of the body, and the first pointed end and the second pointed end being free of barbs, said method comprising:
   (a) at the tissue separation, inserting the barbed tissue connector via the first pointed end into tissue at a position on one side of the tissue separation, wherein the barbed tissue connector comprises a bioabsorbable material;
   (b) repeating step (a) at the other side of the tissue separation, using the second pointed end of the barbed tissue connector, at a position located across the tissue separation from the position in which the first pointed end of the barbed tissue connector was inserted wound; and
   (c) bringing the two tissue portions together by pressing the two tissue portions together or by pushing the barbed tissue connector through the tissue.

61. A device for insertion into tissue comprising:
   a barbed tissue connector having an elongated body, a pointed end, a length, and a substantially polygonal periphery in cross-section including at least three sides, each side meeting an adjacent side at an edge of the elongated body, and a plurality of barbs, each barb projecting from one of the edges of the body, and being disposed around the periphery of the body along at least a portion of the length of the body, the barbs being configured such that they are yieldable in a direction toward the body and resist retraction from tissue in an opposite direction, and
   an inserting device having a closed tubular body, a leading end, and a trailing end, the tubular body being sufficiently long to contain at least a portion of the barbed tissue connector.

62. The device of claim 61, wherein the leading end of the inserting device is tapered inwardly.

63. The device of claim 61, wherein the trailing end of the inserting device is tapered outwardly.

64. The device of claim 61, wherein the tubular body of the inserting device has a circular cross section.

65. The device of claim 61, wherein an inside diameter of the tubular body of the inserting device is slightly less than an outside cross-section of the connector.

66. The device of claim 61, wherein the tubular body of the inserting device is generally arcuate in an axial direction.

67. The device of claim 61, wherein the inserting device has a handle on the tubular body adjacent the trailing end.

68. The device of claim 61, wherein at least one barb of the connector protrudes from the leading end of the tubular body of the inserting device.

69. The device of claim 61, wherein the body of the connector is formed of a material sufficiently hard for the point to pierce tissue and to enable the connector to be inserted in tissue when a substantially axial force is applied to the body of the connector.

70. The device of claim 61, wherein the connector comprises a bioabsorbable material.

71. The device of claim 70, wherein the bioabsorbable material comprises polyglycolic acid polymer, polyglycolic acid copolymer, polylactic acid polymer, or polylactic acid copolymer.

72. The device of claim 61, wherein the connector has the barbs oriented at progressively staggered positions along the edges of the body.

73. The device of claim 61, wherein the barbs have a unidirectional configuration on the connector.

74. The device of claim 61, wherein the connector has the barbs oriented in one direction for a first portion of the length of the body of the connector and in an opposite direction for a second portion of the length of the body of the connector.

75. The device of claim 61, wherein the barbs are arranged in a helical pattern on the connector.

76. The device of claim 61, wherein the pointed end of the connector is free of barbs.

77. The device of claim 61, wherein the connector has an end opposite the pointed end comprising a head end.

78. A device for insertion into tissue comprising:
   an inserting device having a closed tubular body, a leading end, and a trailing end, and
   a barbed tissue connector having an elongated body, a pointed end, a length, and a substantially polygonal periphery in cross-section including at least three sides, each side meeting an adjacent side at an edge of the elongated body, and a plurality of barbs, each barb projecting from one of the edges of the body, and being disposed around the periphery of the body along at least a portion of the length of the body, the barbs being configured such that they are yieldable in a direction toward the body and resist retraction from tissue in an opposite direction, and the connector being positioned in the tubular body of the inserting device with the pointed end of the connector protruding from the leading end of the inserting device.

79. The device of claim 78, wherein the leading end of the inserting device is tapered inwardly.

80. The device of claim 78, wherein the trailing end of the inserting device is tapered outwardly.

81. The device of claim 78, wherein the tubular body of the inserting device has a circular cross section.

82. The device of claim 78, wherein an inside diameter of the tubular body of the inserting device is slightly less than an outside cross-section of the connector.

83. The device of claim 78, wherein the tubular body of the inserting device is generally arcuate in an axial direction.

84. The device of claim 78, wherein the inserting device has a handle on the tubular body adjacent the trailing end.

85. The device of claim 78, wherein at least one barb of the connector protrudes from the leading end of the tubular body of the inserting device.

86. The device of claim 78, wherein the body of the connector is formed of a material sufficiently hard for the point to pierce tissue and enable the connector to be inserted in tissue when a substantially axial force is applied to the body of the connector.

87. The device of claim 78, wherein the connector comprises a bioabsorbable material.

88. The device of claim 87, wherein the bioabsorbable material comprises polyglycolic acid polymer, polyglycolic acid copolymer, polylactic acid polymer, or polylactic acid copolymer.

89. The device of claim 78, wherein the connector has the barbs oriented at progressively staggered positions along the periphery of the body.

90. The device of claim 78, wherein the barbs have a unidirectional configuration on the connector.

91. The device of claim 78, wherein the connector has the barbs oriented in one direction for a first portion of the length of the body of the connector and in an opposite direction for a second portion of the length of the body of the connector.

92. The device of claim 78, wherein the barbs are arranged in a helical pattern on the connector.

93. The device of claim 78, wherein the pointed end of the connector is free of barbs.

94. The device of claim 78, wherein the connector has an end opposite the pointed end comprising a head end.

95. A method for bringing together one side and an other side of an open wound in tissue with a barbed tissue connector, where the barbed tissue connector has an elongated body, and a substantially polygonal periphery in cross-section including at least three sides, each side meeting an adjacent side at an edge of the elongated body, and a plurality of barbs, each barb projecting from one of the edges of the body, the barbs being sized and shaped to resist retraction of the barbed tissue connector from the tissue,
said method comprising:
   (iii) inserting the barbed tissue connector into tissue from one side of the wound,
   (iv) penetrating through tissue on the one side of the wound, and
   (iii) penetrating into tissue at the other side of the wound such that a portion of the body extends from the tissue at the one side of the wound.

96. The method of claim 95, said method comprising:
   (i) inserting another barbed tissue connector from the other side of the wound, where the other barbed tissue connector has an elongated body, and a substantially polygonal periphery in cross-section including at least three sides, each side meeting an adjacent side at an edge of the elongated body, and a plurality of barbs, each barb projecting from one of the edges of the body, the barbs of the other barbed tissue connector being sized and shaped to resist retraction of the other barbed tissue connector from the tissue,
   (ii) penetrating through tissue at the other side of the wound, and
   (vii) penetrating into tissue at the one side of the wound.

97. The method of claim 95, wherein inserting the barbed tissue connector is accomplished with an inserting device.

98. The method of claim 97, wherein the inserting device comprises a tubular body.

99. The method of claim 95, wherein the barbed tissue connector comprises a bioabsorbable material.

100. The method of claim 99, wherein the bioabsorbable material comprises polyglycolic acid polymer, polyglycolic acid copolymer, polylactic acid polymer, or polylactic acid copolymer.

101. The method of claim 95, wherein the barbed tissue connector has the barbs oriented at progressively staggered positions around the periphery of the body.

102. The method of claim 95, wherein the barbed tissue connector has an end that is free of barbs.

103. A surgical method for bringing together two tissue portions on either side of a tissue separation in tissue with a barbed tissue connector, where the barbed tissue connector has an elongated body, a first end, a second end, a length, and a substantially polygonal periphery in cross-section including at least three sides, each side meeting an adjacent side at an edge of the elongated body, and a plurality of barbs, each barb projecting from one of the edges of the body, the barbs being sized and shaped to resist retraction of the barbed tissue connector from the tissue, the barbed tissue connector having the barbs oriented in one direction for a first portion of the length of the body and in an opposite direction for a second portion of the length of the body, said method comprising:
   (a) at the tissue separation, inserting the barbed tissue connector via the first end into tissue at a position on one side of the tissue separation;
   (b) repeating step (a) at the other side of the tissue separation, using the second end of the barbed tissue connector, at a position located across the tissue separation from the position in which the first end of the barbed tissue connector was inserted; and
   (c) bringing the two tissue portions together.

104. The surgical method of claim 103, wherein bringing the two tissue portions together in step (c) is accomplished by pressing the two tissue portions together.

105. The surgical method of claim 103, wherein bringing the two tissue portions together in step (c) is accomplished by pushing the barbed tissue connector through the tissue.

106. The surgical method of claim 103, wherein inserting the barbed tissue connector is accomplished with an inserting device.

107. The surgical method of claim 106, wherein the inserting device comprises a tubular body.

108. The surgical method of claim 103, wherein the two tissue portions comprise two sides of an open wound in skin.

109. The surgical method of claim 103, wherein the barbed tissue connector comprises a bioabsorbable material.

110. The surgical method of claim 109, wherein the bioabsorbable material comprises polyglycolic acid polymer, polyglycolic acid copolymer, polylactic acid polymer, or polylactic acid copolymer.

111. The surgical method of claim 103, wherein the two tissue portions comprise portions of a tendon.

112. The surgical method of claim 103, wherein:
(a) the two tissue portions comprise two sides of an open wound at the skin of a patient, and
(b) the first end and the second end are free of barbs.

113. A surgical method for bringing together two tissue portions on either side of a tissue separation in tissue with a barbed tissue connector, where the barbed tissue connector has an elongated body, and a substantially polygonal periphery in cross-section including at least three sides, each side meeting an adjacent side at an edge of the elongated body, and a plurality of barbs, each barb projecting from one of the edges of the body, the barbs being sized and shaped to resist retraction of the barbed tissue connector from the tissue and permitting movement of the barbed tissue connector through the tissue in the direction the barbed tissue connector is inserted, said method comprising:
(a) at the tissue separation, inserting the barbed tissue connector into tissue at one side of the tissue separation,
(b) penetrating through tissue on the one side of the separation, and
(c) penetrating into tissue on the other side of the separation such that a portion of the body extends from the tissue at the one side of the tissue separation.

114. The surgical method of claim 113, said method comprising:
(d) inserting another barbed tissue connector from the other side of the tissue separation, where the other barbed tissue connector has an elongated body, and a substantially polygonal periphery in cross-section including at least three sides, each side meeting an adjacent side at an edge of the elongated body, and a plurality of barbs, each barb projecting from one of the edges of the body, the barbs of the other barbed tissue connector being sized and shaped to resist retraction of the other barbed tissue connector from the tissue and permitting movement of the other barbed tissue connector through the tissue in the direction the other barbed tissue connector is inserted,
(e) penetrating through tissue on the other side of the of the separation, and
(f) penetrating into tissue on the one side of the separation.

115. The surgical method of claim 113, wherein the two tissue portions comprise sections of a tendon.

116. The surgical method of claim 113, wherein the two tissue portions comprise two sides of an open wound in skin.

117. The surgical method of claim 113, wherein the barbed tissue connector comprises a bioabsorbable material.

118. The surgical method of claim 117, wherein the bioabsorbable material comprises polyglycolic acid polymer, polyglycolic acid copolymer, polylactic acid polymer, or polylactic acid copolymer.

119. A surgical method for inserting a barbed tissue connector into tissue, where the barbed tissue connector has an elongated body, an end adapted to penetrate the tissue, an opposite end, and a substantially polygonal periphery in cross-section including at least three sides, each side meeting an adjacent side at an edge of the elongated body, and a plurality of barbs, each barb projecting from one of the edges of the body, the barbs being sized and shaped to resist retraction of the barbed tissue connector from the tissue, said method comprising inserting the penetrating end into tissue by applying force to the opposite end such that a portion of the body extends from the tissue.

120. The surgical method of claim 119, wherein the opposite end comprises a head end.

121. The surgical method of claim 119, wherein after an adequate amount of time has passed for healing, depressing the tissue beneath the head end and cutting the head end from the elongated body, permitting the tissue to rise up over the cut end of the elongated body.

122. The surgical method of claim 119, wherein inserting the barbed tissue connector is accomplished with an inserting device.

123. The surgical method of claim 122, wherein the inserting device comprises a tubular body.

124. The surgical method of claim 119, wherein the barbed tissue connector comprises a bioabsorbable material.

125. The surgical method of claim 124, wherein the bioabsorbable material comprises polyglycolic acid polymer, polyglycolic acid copolymer, polylactic acid polymer, or polylactic acid copolymer.

126. A method for bringing together one side and an other side of an open wound in tissue with a barbed tissue connector, where the barbed tissue connector has an elongated body, and a substantially polygonal periphery in cross-section including at least three sides, each side meeting an adjacent side at an edge of the elongated body, and a plurality of barbs, each barb projecting from one of the edges of the body, the barbs being sized and shaped to resist retraction of the barbed tissue connector from the tissue, said method comprising:
(v) inserting the barbed tissue connector into tissue from one side of the wound,
(vi) penetrating through tissue on the one side of the wound,
(vii) penetrating into tissue at the other side of the wound such that a portion of the body extends from the tissue at the one side of the wound,
(viii) inserting another barbed tissue connector, where the other barbed tissue connector has an elongated body, a periphery, and a plurality of closely spaced barbs which extend around the periphery of the body, the barbs of the other barbed tissue connector being sized and shaped to resist retraction of the other barbed tissue connector from the tissue, from the other side of the wound,
(vii) penetrating through tissue at the other side of the wound, and
(viii) penetrating into tissue at the one side of the wound such that a portion of the body of the another barbed tissue connector extends from the tissue at the other side of the wound.

127. A surgical method for bringing together two tissue portions on either side of a tissue separation in tissue with a barbed tissue connector, where the barbed tissue connector has an elongated body, a first end, a second end, and a substantially polygonal periphery in cross-section including at least three sides, each side meeting an adjacent side at an edge of the elongated body, and a plurality of barbs, each barb projecting from one of the edges of the body, the barbs being sized and shaped to resist retraction of the barbed tissue connector from the tissue, the barbed tissue connector having the barbs oriented in one direction for a first portion of the length of the body and in an opposite direction for a second portion of the length of the body, and the first end and the second end being free of barbs, said method comprising:

(d) at the tissue separation, inserting the barbed tissue connector via the first end into tissue at a position on one side of the tissue separation, wherein the barbed tissue connector comprises a bioabsorbable material;

(e) repeating step (a) at the other side of the tissue separation, using the second end of the barbed tissue connector, at a position located across the tissue separation from the position in which the first pointed end of the barbed tissue connector was inserted wound; and (f) bringing the two tissue portions together by pressing the two tissue portions together or by pushing the barbed tissue connector through the tissue.

128. A device for insertion into tissue comprising:
a barbed tissue connector having an elongated body, a pointed end, a length, and a substantially polygonal periphery in cross-section including at least three sides, each side meeting an adjacent side at an edge of the elongated body, and a plurality of barbs, each barb projecting from one of the edges of the body, and being disposed around the periphery of the body along at least a portion of the length of the body, the barbs being configured such that they are yieldable in a direction toward the body and resist retraction from tissue in an opposite direction, and an inserting device having a closed tubular body, a leading end, and a trailing end, the tubular body being sufficiently long to contain at least a portion of the barbed tissue connector.

129. The device of claim 128, wherein the leading end of the inserting device is tapered inwardly.

130. The device of claim 128, wherein the trailing end of the inserting device is tapered outwardly.

131. The device of claim 128, wherein the tubular body of the inserting device has a circular cross section.

132. The device of claim 128, wherein an inside diameter of the tubular body of the inserting device is slightly less than an outside cross-section of the connector.

133. The device of claim 128, wherein the tubular body of the inserting device is generally arcuate in an axial direction.

134. The device of claim 128, wherein the inserting device has a handle on the tubular body adjacent the trailing end.

135. The device of claim 128, wherein at least one barb of the connector protrudes from the leading end of the tubular body of the inserting device.

136. The device of claim 128, wherein the body of the connector has a pointed end formed of a material sufficiently hard for the pointed end to pierce tissue and to enable the connector to be inserted in tissue when a substantially axial force is applied to the body of the connector.

137. The device of claim 128, wherein the connector comprises a bioabsorbable material.

138. The device of claim 137, wherein the bioabsorbable material comprises polyglycolic acid polymer, polyglycolic acid copolymer, polylactic acid polymer, or polylactic acid copolymer.

139. The device of claim 128, wherein the connector has the barbs oriented at progressively staggered positions around the periphery of the body.

140. The device of claim 128, wherein the barbs have a unidirectional configuration on the connector.

141. The device of claim 128, wherein the connector has the barbs oriented in one direction for a first portion of the length of the body of the connector and in an opposite direction for a second portion of the length of the body of the connector.

142. The device of claim 128, wherein the barbs are arranged in a helical pattern on the connector.

143. The device of claim 128, wherein the connector has an end free of barbs.

144. The device of claim 128, wherein the connector has an end and an opposite end that comprises a head end.

145. A device for insertion into tissue comprising:
an inserting device having a tubular body, a leading end, and a trailing end, and a barbed tissue connector having an elongated body, a length, and a substantially polygonal periphery in cross-section including at least three sides, each side meeting an adjacent side at an edge of the elongated body, and a plurality of barbs, each barb projecting from one of the edges of the body, and being disposed around the periphery of the body along at least a portion of the length of the body, the barbs being configured such that they are yieldable in a direction toward the body and resist retraction from tissue in an opposite direction, and the connector being positioned in the tubular body of the inserting device with one end of the connector protruding from the leading end of the inserting device.

146. The device of claim 145, wherein the leading end of the inserting device is tapered inwardly.

147. The device of claim 145, wherein the trailing end of the inserting device is tapered outwardly.

148. The device of claim 145, wherein the tubular body of the inserting device has a circular cross section.

149. The device of claim 145, wherein an inside diameter of the tubular body of the inserting device is slightly less than an outside cross-section of the connector.

150. The device of claim 145, wherein the tubular body of the inserting device is generally arcuate in an axial direction.

151. The device of claim 145, wherein the inserting device has a handle on the tubular body adjacent the trailing end.

152. The device of claim 145, wherein at least one barb of the connector protrudes from the leading end of the tubular body of the inserting device.

153. The device of claim 145, wherein the body of the connector is formed of a material sufficiently hard for the point to pierce tissue and enable the connector to be inserted in tissue when a substantially axial force is applied to the body of the connector.

154. The device of claim 145, wherein the connector comprises a bioabsorbable material.

155. The device of claim 145, wherein the bioabsorbable material comprises polyglycolic acid polymer, polyglycolic acid copolymer, polylactic acid polymer, or polylactic acid copolymer.

156. The device of claim 145, wherein the connector has the barbs oriented at progressively staggered positions along the edges of the body.

157. The device of claim 145, wherein the barbs have a unidirectional configuration on the connector.

158. The device of claim 145, wherein the connector has the barbs oriented in one direction for a first portion of the length of the body of the connector and in an opposite direction for a second portion of the length of the body of the connector.

159. The device of claim 145, wherein the barbs are arranged in a helical pattern on the connector.

160. The device of claim 145, wherein one end of the connector is free of barbs.

161. The device of claim 145, wherein the connector has an end and an opposite end comprising a head end.

162. A method for inserting a barbed tissue connector in tissue, where the barbed tissue connector has an elongated body, and a substantially polygonal periphery in cross-section including at least three sides, each side meeting an adjacent side at an edge of the elongated body, and a plurality of barbs, each barb projecting from one of the edges of the body, and being disposed around the periphery of the body along at least a portion of the length of the body, the barbs being sized and shaped to resist retraction of the barbed tissue connector from the tissue, said method comprising:
  (i) positioning the barbed tissue connector in an inserting device including a closed tubular body,
  (ii) inserting the inserting device into tissue, and
  (iii) extracting the inserting device from the tissue while leaving the connector in the tissue.

163. The method of claim 162, said method comprising:
  (iv) repeating steps (i), (ii), and (iii) with another barbed tissue connector, where the other barbed tissue connector has an elongated body, and a substantially polygonal periphery in cross-section including at least three sides, each side meeting an adjacent side at an edge of the elongated body, and a plurality of barbs, each barb projecting from one of the edges of the body, and being disposed around the periphery of the body along at least a portion of the length of the body, the barbs of the other barbed tissue connector being sized and shaped to resist retraction of the other barbed tissue connector from the tissue.

164. The method of claim 162, wherein the barbed tissue connector comprises a bioabsorbable material.

165. The method of claim 164, wherein the bioabsorbable material comprises polyglycolic acid polymer, polyglycolic acid copolymer, polylactic acid polymer, or polylactic acid copolymer.

166. The method of claim 162, wherein the barbed tissue connector has the barbs oriented at progressively staggered positions around the periphery of the body.

167. The method of claim 162, wherein the barbed tissue connector has an end that is free of barbs.

168. The method of claim 162, wherein the body of the connector has a pointed end formed of a material sufficiently hard for the pointed end to pierce tissue and to enable the connector to be inserted in tissue when a substantially axial force is applied to the body of the connector.

169. The method of claim 162, wherein the connector has the barbs oriented at progressively staggered positions around the periphery of the body.

170. The method of claim 162, wherein the barbs have a unidirectional configuration on the connector.

171. The method of claim 162, wherein the connector has the barbs oriented in one direction for a first portion of the length of the body of the connector and in an opposite direction for a second portion of the length of the body of the connector.

172. The method of claim 162, wherein the barbs are arranged in a helical pattern on the connector.

173. The method of claim 162, wherein the connector has an end free of barbs.

174. The method of claim 162, wherein the connector has an end and an opposite end that comprises a head end.

175. The method of claim 162, wherein the tubular body of the inserting device has a circular cross section.

176. The method of claim 162, wherein an inside diameter of the tubular body of the inserting device is slightly less than an outside diameter of the connector.

177. The method of claim 162, wherein the tubular body of the inserting device is generally arcuate in an axial direction.

178. The method of claim 162, wherein the inserting device has a leading end and at least one barb of the connector protrudes from the leading end.

179. The method of claim 162, wherein the inserting device has a leading end that is tapered inwardly.

180. The method of claim 162, wherein the inserting device has a trailing end that is tapered outwardly.

181. The method of claim 162, wherein the inserting device has a trailing end and a handle adjacent the trailing end.

\* \* \* \* \*